US007517312B2

(12) United States Patent
Loeb et al.

(10) Patent No.: US 7,517,312 B2
(45) **Date of Patent: *Apr. 14, 2009**

(54) EXTERNAL COUNTER PULSATION TREATMENT

(75) Inventors: Marvin P. Loeb, Huntington Beach, CA (US); Ginger Johnson, Newport Beach, CA (US); John P. Burrell, Tustin, CA (US); Robert J. Sullivan, Lake Forest, CA (US); Lawrence J. Perkins, Anaheim, CA (US)

(73) Assignee: Cardiomedics, Inc., Lake Forest, CA (US)

( * ) Notice: Subject to any disclaimer, the term of this patent is extended or adjusted under 35 U.S.C. 154(b) by 684 days.

This patent is subject to a terminal disclaimer.

(21) Appl. No.: 10/938,155

(22) Filed: Sep. 10, 2004

(65) Prior Publication Data

US 2005/0177078 A1 Aug. 11, 2005

(51) Int. Cl.
*A61N 1/362* (2006.01)

(52) U.S. Cl. ........................................................ 600/16

(58) Field of Classification Search .................... 600/16
See application file for complete search history.

(56) References Cited

U.S. PATENT DOCUMENTS

2003/0216651 A1* 11/2003 Burns et al. ................. 600/483

* cited by examiner

*Primary Examiner*—Carl H Layno
*Assistant Examiner*—Eric D Bertram
(74) *Attorney, Agent, or Firm*—Olson & Cepuritis, Ltd.

(57) ABSTRACT

A method for treating patients suffering from left ventricular dysfunction, exhibited by a left ventricular ejection fraction (LVEF) less than normal, is disclosed. The method involves applying, during diastole, for a time period of about one hour, about five days each week for at least about seven weeks, an incrementally increasing therapeutic pressure to the patients' lower extremities, from the calves through the thighs and the buttocks. The hourly treatments are carried out at incrementally increasing peak diastolic/systolic pressure ratios (D/S Ratios) in the range of about 0.4:1 up to about 0.6:1 and thereafter at a D/S Ratio in the range of 0.5:1 to 1:1 for each consecutive hourly treatment, with the proviso that the average D/S Ratio over the entire treatment regimen does not exceed about 0.9:1.

13 Claims, No Drawings

EXTERNAL COUNTER PULSATION TREATMENT

CROSS-REFERENCE TO RELATED APPLICATIONS

Related application U.S. Ser. No. 10/681,812 filed on Oct. 7, 2003 is now U.S. Pat. No. 7,244,255 B2. U.S. Ser. No. 10/263,954, filed on Oct. 2, 2002, a related application, has become abandoned.

FIELD OF INVENTION

This invention relates to a non-invasive treatment for congestive heart failure and other conditions typified by a low left ventricular ejection fraction (LVEF).

BACKGROUND OF INVENTION

External Counter Pulsation (ECP) is a safe and effective, non-invasive treatment to assist circulation, particularly in the treatment of ischemic heart disease. "Counter Pulsation" improves heart function by increasing blood flow through the coronary vessels using a series of cuffs, fastened about the legs and buttocks, which contain inflatable bladders.

"External" means that the treatment is applied to the exterior of the of the patient's body. Surgery is not required.

The treatment system compresses the legs from the calves through the thighs, and the buttocks, sequentially by inflating sets of bladders encased in flexible, fabric cuffs during the resting phase of the heart cycle (diastole). This results in the movement of blood from the legs toward the heart through both the arterial and the venous systems.

Each wave of pressure is electronically timed to a heart beat, so that the increased blood flow is delivered to the heart during the time period the heart is relaxing (diastole). Before the heart begins to contract again (systole), the pressure is rapidly released. This lowers resistance in the blood vessels of the legs so that blood may be pumped more easily from the heart, decreasing the amount of work required of the heart muscle. This is evidenced by a reduction in the patient's systolic pressure.

The aortic valve is the heart valve through which blood leaves the left ventricle, the main pumping chamber of the heart, and which prevents back flow into the left ventricle. The coronary arteries open off the aorta, above the aortic valve, and the pressure applied to the lower extremities drives extra blood into the aorta and through the coronary arteries, expanding the heart's networks of tiny auxiliary blood vessels. This is evidenced by the increase in the patient's diastolic pressure. The volume of blood flowing to the heart muscle is thus increased. Blood forced up the veins enters the right chambers of the heart. This is called "pre-loading" of the heart.

The typical ECP treatment regimen for chronic angina patients is 35 hours of treatment, usually one hour per day, five days per week for seven weeks. While not as desirable as the above-regimen, a 2-hour per day regimen can also be utilized, which reduces the time to completion to 3½ weeks. In the treatment of heart attacks, ECP can be administered for up to four hours, with a 10 minute rest period after each hour of treatment. Pressure is typically applied to produce a peak diastolic pressure to peak systolic pressure ratio (D/S Ratio) of 1.5:1 to 2:1 or higher in the treatment of chronic angina and heart attacks. The duration of treatment and rest intervals depend on the patient's condition, the degree of augmentation of diastolic pressure to systolic pressure obtained, patient tolerance and the like indications.

Congestive heart failure (CHF) affects an estimated two-and-one-half million people in the United States and causes approximately 400,000 deaths per year, a number almost equal to the deaths from all types of cancer combined. Other than implantable defibrillators and dual chamber, cardiac "resynchronization" pacemakers, which are extremely expensive (implantation of such a device in the U.S. currently costs $50,000 or more), require surgery and have shown only a reduction in mortality of about 50% from the American Heart Association's 18.8% annual mortality from CHF in the United States, there is presently no truly effective therapy for CHF.

It has now been found that ECP can be advantageously utilized to treat patients suffering from congestive heart failure and left ventricular dysfunction. Such patients frequently exhibit a left ventricular ejection fraction of 40 percent or less by volume (about 55 percent is normal), because the diseased heart is not able to pump with sufficient force to efficiently eject blood from the main pumping ventricle of the heart.

Currently practiced ECP methods, such as used in the treatment of chronic angina and heart attacks (i.e. at D/S Ratio of 1.5:1 to 2:1 or higher), however, can cause excessive preloading of the heart, and the heart cannot pump out or "eject" a sufficient amount of blood. This causes blood to "pool" in the blood vessels of the lungs, abdomen and extremities, as well as fluid to build-up in the lungs, calves, ankles and feet. The heart muscle necessarily works harder and thickens, which further reduces its pumping efficiency. As a result, more fluid builds up in the lungs, making it difficult for the patient to breathe. A recurrence or worsening of heart failure or even death can result. The present method, however, avoids such undesirable consequences and leads to a substantial long-term reduction in mortality and an improvement in the condition and quality of life of the patient.

SUMMARY OF THE INVENTION

The present method is eminently well suited for treating patients exhibiting left ventricular dysfunction and having a left ventricular ejection fraction of less than about 40 percent. The method comprises the daily application of external therapeutic pressure to the lower extremities of a patient during diastole, i.e., during the resting phase of the cardiac cycle. The external therapeutic pressure is applied sequentially to lower extremities of the patient, i.e., first to the patient's calves, next to the patient's thighs, and then to the patient's buttocks. The present method can be used to treat congestive heart failure, cardiomyopathy, post-heart transplant cardiac dysfunction, post-cardiac arrest cardiac dysfunction, heart trauma, heart infection, post-acute myocardial infarction cardiac dysfunction, and the like.

The treatment regimen for CHF patients with an ejection fraction of no more than about 40% but at least 15% comprises applying daily, about five days each week for at least about seven weeks for a time period of about one hour, during diastole, incrementally increasing external therapeutic pressure to initially produce a daily D/S Ratio in the range of at least about 0.4:1 up to about 0.6:1 and thereafter a daily D/S Ratio in the range of about 0.5:1 to about 1:1 with the proviso that the average daily D/S Ratio during the course of the treatment does not exceed about 0.9:1.

DETAILED DESCRIPTION OF PREFERRED EMBODIMENT

Abbreviations and Acronyms

ECP=external counterpulsation
CCSF=Canadian Society Function
CHF=congestive heart failure
D/S Ratio=peak diastolic to peak systolic pressure ratio
LVEF=left ventricular ejection fraction
NYHA=New York Heart Association
CABG=coronary artery bypass "Congestive heart failure" is a condition in which the heart cannot pump enough blood to the lungs and body's other organs, which in turn leads to fluid retention. This condition can result, inter alia, from either diastolic or systolic dysfunction. Heart failure of diastolic etiology is more common.

"Left ventricular ejection fraction (LVEF)" as used herein and in the appended claims is the percentage of the end diastolic volume of blood ejected during systole and is calculated as follows:

$$\text{LVEF} = \frac{\text{end diastolic volume} - \text{end systilic volume}}{\text{end diastolic volume}} \times 100$$

In the data reported hereinbelow, LVEF was assessed using echocardiography pre- and one-year post treatment.

External Counter Pulsation (ECP) is a non-invasive version of the intra-aortic balloon pump. ECP is utilized in the present method to move a relatively large volume of blood while decreasing cardiac workload (systolic pressure) and increasing diastolic pressure.

When ECP is administered to CHF patients at the compression pressures, delay times and compression durations common to the treatment of Angina (usually at a D/S Ratio of 1.5:1 to 2:1 or larger), some CHF patients, particularly those with relatively low ejection fractions, cannot eject the added volume of blood from their heart. Some patients do well for the first 5 to 10 hours of ECP therapy at such D/S Ratios, but thereafter their CHF symptoms worsen, they may require hospitalization and death can result.

These problems can be avoided by maintaining the D/S Ratio during the initial one-hour treatment of the 35 one-hour, daily ECP treatments to a range of about 0,4:1 up to about 0.6:1, with the relatively lower D/S Ratios used in patients with very low ejection fractions, i.e., about 15% to 20%. ECP at somewhat higher D/S Ratios near the same range is then applied during the following 4 hours of ECP, and slightly higher D/S Ratios are applied during the next 15 hours of ECP. Slightly higher D/S Ratios are then applied during the remaining 15 hours of the 35 hours of ECP therapy. However, the average D/S Ratio over the 35 hour course of ECP therapy preferably is less than 0.8:1 for CHF patients with ejection fractions of 30% or less. This regimen, utilizing a gradual increase in D/S Ratio from an uncommonly low, starting level, is known as the HeartSmart™ Graduated ECP Regimen (Cardiomedics, Inc, Irvine, CA).

CHF patients with an ejection fraction less than 15% are in an extremely fragile condition and are ordinarily not suitable candidates for ECP.

If the CHF patient has an ejection fraction of 15% to 20%, in addition to optimal timing of compression, ECP more preferably is applied at a pressure of up to about 90-120 mmHg to produce a D/S Ratio of about 0.4:1 for the first hour of ECP, next pressure is increased to about 120-150 mmHg to produce a D/S Ratio of about 0.5:1 for the next 4 hours of ECP, thereafter pressure is increased to maintain a D/S Ratio of about 0.7:1 for the next 15 hours of ECP, and then pressure is increased as needed to maintain a D/S Ratio of 0.8:1 for the next 15 hours of treatment, i.e., the balance of the 35 hour Graduated ECP Pressure Regimen, for an average D/S Ratio of about 0.63:1, thereby training the heart to gradually eject a greater volume of blood.

If the CHF patient's ejection fraction is 20% to 30%, in addition to optimal timing of compression, ECP more preferably is applied at up to about 90-120 mmHg of pressure to produce a D/S Ratio of about 0.5:1 for the first hour of ECP, next pressure is increased to about 120-150 mmHg to produce a D/S Ratio of about 0.6:1 for the next four hours of ECP, thereafter pressure is increased sufficient to maintain a D/S Ratio of about 0.7:1 for the next 15 hours of ECP, and then pressure is increased as needed to maintain a D/S Ratio of about 0.8:1 for the next 15 hours of treatment, i.e., the remainder of the 35 hour or longer Graduated ECP Pressure Regimen, for an average D/S Ratio of about 0.73:1, producing the same training effect on the heart.

If the CHF patient's ejection fraction is 30% to 40%, in addition to optimal timing of compression, ECP more preferably is applied at a pressure of up to about 90-120 mmHg to produce a D/S Ratio of about 0.6:1 for the first hour of ECP, next pressure is increased to produce a D/S Ratio of about 0.7:1 for the next four hours of ECP, thereafter pressure is increased to maintain a D/S Ratio of about 0.8:1 for the next 15 hours of ECP, and then the pressure is increased as needed to maintain a D/S Ratio of about 0.9:1 for the next 15 hours of ECP, for an average D/S Ratio of about 0.83:1.

Some CHF patients may require more than 35 hours of ECP, some up to about 60 hours, or more.

We have found that ECP, applied by gradually increasing the D/S Ratio, causes a "training effect" on the heart, resulting in its beating more synchronously (similar to the effect of a dual chamber, cardiac resynchronization pacemaker) and creates angiogenesis, endothelial cell remodeling, release of nitrous oxide and other benefits of ECP. As the heart grows stronger and beats more efficiently, it can accept and eject successively larger volumes of blood.

Treatment and Follow-Up. Data from the Cardiomedics ECP Patient Registry (sponsored by Cardiomedics, Inc. Irvine, Calif., USA) was used to examine the benefit and safety of ECP treatment with the sponsor's CardiAssist™ ECP System in 130 patients with NYHA Class I-IV CHF and concomitant CCSF Class III or IV angina pectoris (Angina) over a period of one year. All of the patients received 35 ECP treatments (one-hour per day, 5 days a week over a seven-week period). The study included both male (104) and female (26) patients (age range 47-88). CCSF Class IV Angina was seen only in the NYHA Class IV CHF patients. All descriptive statistics are shown as means±1 SD.

Data was also analyzed on subgroups of 54, 40 and 36 patients who were treated at an average D/S Ratio of 0.7:1 (range 0.4 to 0.99:1), 1.08:1 (range 1.0 to 1.29:1), and 1.32:1 (range 1.3 to 1.6:1), respectively. In the 54 and 40 patient subgroups, ECP was applied pursuant to a proprietary ECP treatment protocol in which the ECP treatments were begun at low D/S Ratios and gradually increased to take advantage of ECP's "training effect" on the heart, which enables the heart to eject successively larger volumes of blood, versus the subgroup of 43 patients who were treated at an average D/S Ratio of 1.32:1 (range 1.30:1 to 1.60:1), which are used in the treatment of angina.

Data on the enrolled patients was collected at six clinical sites in the United States and entered into a standardized Excel® database. The final dataset was merged and transferred to a SPSS Version 12.0 statistical package. Data was analyzed on each group of CHF patients and comparisons made pre- and one-year post treatment. Measurements were expressed as mean±standard deviation. Individual variable differences from baseline to the end of the study period were determined, using the student t-test for numerical variables and the chi square test for categorical variables with significance at p<0.05.

Baseline Data:

Baseline characteristics of the three groups and the group as a whole are shown in Table I, below.

Of the 54 CHF patients in the Low D/S Ratio Group, 79.6% were male, and the mean age was 68.2±15.6. None (0%) had NYHA Class I CHF, 6 (11.1%) had Class II CHF, 42 (77.7%) had Class III CHF and 6 (11.1%) had Class IV CHF. 76.8% also had CCSF Class III Angina, and 24.3% also had CCSF Class IV Angina. Mean LVEF prior to ECP therapy was 32.6%±7%. History of CABG was present in 75.9% and PTCA in 90.7%.

Of the 40 CHF patients in the Mid D/S Ratio Group, 80.0% were male, and the mean age was 69.7±18.6. One (2.5%) had NYHA Class I CHF, 9 (22.5%) had Class II CHF, 24 (60.0%) had Class III CHF and 6 (15.0%) had Class IV CHF. 79.8% also had CCSF Class III Angina, and 14.3% also had CCSF Class IV Angina. Mean LVEF prior to ECP therapy was 31.3%±11%. History of CABG was present in 69.6% and PTCA in 90.7%.

Of the 36 CHF patients in the High D/S Ratio Group, 80.5% were male, and the mean age was 69.7±22.4. Two (5.5%) had NYHA Class I CHF, 13 (36.1%) had Class II CHF, 15 (41.6%) had Class III CHF and 6 (16.6%) had Class IV CHF. 74.5% also had CCSF Class III Angina, and 19.3% also had CCSF Class IV Angina. Mean LVEF prior to ECP therapy was 32.6%±20%. History of CABG was present in 78.9% and PTCA in 80.9%. All of the patients in the High D/S Ratio Group received medical therapy in accordance with accepted clinical practice.

All of the 130 patients received medical therapy in accordance with accepted clinical practice. None of the 130 patients had an LVEF exceeding 40% or less than 20%, and only three of the 130 patients were in NYHA Class I.

TABLE I

Baseline Characteristics

| | 54 Patients Low D/S Ratio Group | 40 Patients Mid D/S Ratio Group | 36 Patients High D/S Ratio Group |
|---|---|---|---|
| Average Age (yr): | 68.2 ± 15.6 | 69.7 ± 18.6 | 69.7 ± 22.4 |
| Gender: Male | 43 (79.6%) | 32 (80.0%) | 29 (80.5%) |
| Female | 11 (20.4%) | 8 (20.0%) | 7 (19.4%) |
| History of CABG: | 75.9% | 69.6% | 78.9% |
| History of PTCA: | 90.7% | 83.4% | 80.9% |
| Ejection Fraction: | 33% ± 7% | 31% ± 11% | 33% ± 20% |
| NYHA CHF Class I: | 0 (0%) | 1 (2.5%) | 2 (5.5%) |
| NYHA CHF Class II: | 6 (11.1%) | 9 (22.5%) | 13 (36.1%) |
| NYHA CHF Class III: | 42 (77.7%) | 24 (60.0%) | 15 (41.6%) |
| NYHA CHF Class IV: | 6 (11.1%) | 6 (15.0%) | 6 (16.6%) |
| ACE Inhibitors: | 81.5% | 55.0% | 74.4% |
| Beta Blockers: | 31.4% | 30.3% | 23.3% |
| Diuretics: | 68.5% | 55.0% | 75.0% |
| CC Blockers: | 11.1% | 15.2% | 9.3% |
| Nitroglycerin: | 66% | 62% | 61% |

Results:

Mortality: In the year following completion of the ECP therapy, of the 54 CHF patients in the Low D/S Ratio Group (average D/S Ratio 0.7:1), one (1.85%) died. Of the 40 CHF patients in the Mid D/S Ratio Group (average D/S Ratio 1.08:1), three (7.50%) died, and of the 36 CHF patients in the High D/S Ratio Group (average D/S Ratio 1.32:1), three (8.33%) died. Of the 130 patient group as a whole, seven (5.40%) died.

Mortality in the Low D/S Ratio Group of 1.85% was 90% less than the 18.8% annual mortality in NYHA Class I-IV CHF historical controls reported by the American Heart Association's 2002 Heart Failure and Stroke Statistical Update-2002, and 78.2% less than the 8.5 mortality (adjusted to a one-year period) reported in the Madit II Study (Moss, A. et al., Multicenter Automatic Defibrillator Implantation Trial II Investigators: Prophylactic implantation of a defibrillator in patients with myocardial infarction and reduced ejection fraction, N. Eng. J. Med. 2002; 346:877-883), which excluded NYHA Class IV CHF patients, who typically experience higher mortality.

The differences in mortality between the Low D/S Ratio Group to the Mid D/S Ratio Group, High D/S Ratio Group, the 130 patient group as a whole, the 8.5% annualized mortality of the above Madit II Study and the 18.8% mortality of the Heart Failure and Stroke Statistical Update were statistically significant (p<0.0001).

While the differences in mortality in the Mid D/S Ratio and High D/S Ratio Groups and the 130 patient group as a whole were comparable to the mortality of the Heart Failure and Stroke Statistical Update, there was no statistical difference compared to the mortality of the above Moss Study.

Ejection Fraction: LVEF was assessed by echocardiography pre- and one-year post ECP treatment. Of the 53, 37 and 33 surviving patients in the Low, Mid and High D/S Ratio Groups and the 123 surviving patients of the group as a whole, LVEFs improved by 23.0%, 20.1%, 17.5% and 20.4%, respectively, one year after ECP therapy, from a mean of 32.6% to 40.1%, 31.3% to 37.5%, 32.6% to 38.3% and 32.3% to 38.9%, respectively. The difference in LVEFs in all three sub-groups and the entire 123 surviving patients were statistically significant (p<0.05). See Table II, below.

TABLE II

LVEF of Surviving Patients

| Group | TX Prior to ECP | One Year Post ECP Tx | % Change | p Value |
|---|---|---|---|---|
| Low D/S Ratio (53) | 32.6% ± 7.2 | 40.1% ± 26.9 | +23.0 | <.05 |
| Mid D/S Ratio (37) | 31.3% ± 11.6 | 37.5% ± 27.5 | +20.1 | NS |
| High D/S Ratio (33) | 32.6% ± 20.4 | 38.3% ± 14.7 | +17.5 | NS |
| Overall (123) | 32.3% ± 19.7 | 38.9% ± 28.1 | +20.4 | <.05 |

NYHA CHF Class: Of the 53 surviving patients in the Low D/S Ratio Group, NYHA Class improved by an average of 36.6% from a mean Class 3.0±1.0 pre-treatment to a mean Class 1.9±0.5 one year after ECP treatment (p<0.0001). Of the 37 surviving patients in the Mid D/S Ratio Group, NYHA Class improved by an average of 29.6% from a mean Class of 2.7±1.3 pre-treatment to a mean Class of 1.9±0.5 one year after ECP treatment (p<0.005). Of the 33 surviving patients in the High D/S Ratio Group, NYHA Class improved by an average of 29.6% from a mean Class of 2.7±1.3 pre-treatment to a mean Class of 1.9±0.5 one year after ECP treatment (p<0.001). The differences in NYHA Classes in all three of the sub-groups and the entire 123 surviving patients were statistically significant (p<0.005). See Table III, below.

TABLE III

CHF Classification of Surviving Patients

| Group | Class Pre Tx | One Year Post ECP Tx | % Change | p Value |
|---|---|---|---|---|
| Low D/S Ratio (53) | 3.0 ± 1.0 | 1.9 ± .5 | −36.6 | <.0001 |
| Mid D/S Ratio (37) | 2.7 ± 1.3 | 1.9 ± .5 | −29.8 | <.005 |
| High D/S Ratio (33) | 2.7 ± 1.3 | 1.9 ± .5 | −29.6 | <.01 |
| Overall (123) | 2.9 ± 1.1 | 1.8 ± .6 | −28.7 | <.001 |

Hospitalizations: Of the 54 Low D/S Ratio Group patients, the average incidence of all cause hospitalization, including terminal hospitalizations, was reduced by 85.7% from a mean admission rate of 2.8 per patient in the year prior to ECP treatment to 0.4 per patient in the following year. Of the 40 Mid D/S Ratio Group patients, the average incidence of all cause hospitalization, including terminal hospitalizations, was reduced by 82.6% from a mean admission rate of 2.3 per patient in the year prior to ECP treatment to 0.4 per patient in the following year. Of the 36 High D/S Ratio Group patients, the average incidence of all cause hospitalization, including terminal hospitalizations, was reduced by 57.1% from a mean admission rate of 1.4 per patient in the year prior to ECP treatment to 0.6 per patient in the following year. The overall incidence of all cause hospitalization, including terminal hospitalizations, in the 130 patient group as a whole was reduced by an average of 70.0% from a mean admission rate of 1.8 per patient in the year prior to ECP treatment to 0.54 per patient in the following year. The differences in hospitalization between all three of the sub-groups and the 130 patient group as a whole were statistically significant (p value<0.01 or less). See Table IV, below.

TABLE IV

Annual Average Number of All Cause Hospital Admissions Per Patient*

| Group | One Yr Prior to ECP Tx | One Yr Post ECP Tx | % Change | p Value |
|---|---|---|---|---|
| Low D/S Ratio (54) | 2.8 ± 1.6 | 0.4 ± .5 | −85.7 | <.0001 |
| Mid D/S Ratio (40) | 2.3 ± 1.4 | 0.4 ± .5 | −82.6 | <.0001 |
| High D/S Ratio (36) | 1.4 ± 1.7 | 0.6 ± .5 | −57.1 | <.01 |
| Overall (130) | 1.8 ± 1.3 | 0.54 ± .5 | −70.0 | <.001 |

*Includes terminal hospitalizations.

At one year after ECP treatment regimen there was observed a significant increase in mean LVEF from baseline as well as a significant reduction from baseline in mean NYHA CHF Class and a significant reduction in the average incidence of hospital admissions.

The foregoing data also indicates that ECP, particularly if administered under the HeartSmart™ Graduated Low D/S Ratio ECP Regimen described above, is safe and efficacious for the treatment of congestive heart failure. ECP, administered at Low D/S Ratios, under the above-described regimen, significantly reduced mortality, compared to published data and that of the Mid and High D/S Ratio Groups and the 130 patient group as a whole, and significantly increased left ventricular systolic function, as determined by echocardiography. Such patient benefits may also have a significant impact on the overall treatment costs for heart failure.

Other conditions which will benefit from the above described Graduated, Low D/S Ratio ECP Regimen include cardiomyopthy (weakening of the heart muscle of uncertain etiology), heart transplant candidates waiting for a biocompatible donor heart (many of whom die before a biocompatible donor heart becomes available), post-heart transplantation cardiac dysfunction (due to damage to the donor heart in explanation, transit and implantation), post cardiac arrest cardiac dysfunction (due to the absence of blood flow and damage to the heart due to oxygen deprivation), post-acute myocardial infarction cardiac (AMI) dysfunction (due to damage to the heart wall from lack of blood flow and oxygenation) and other forms of left ventricular dysfunction, including without limitation wounds to and infections in the heart. In all of the foregoing, the heart cannot effectively eject a sufficient percentage of the blood in the left ventricle. The aforementioned Graduated, Low D/S Ratio ECP Regimen can train the heart to beat more synchronously and accept and eject increasing volumes of blood, safely and effectively treating those conditions.

The discussion and data presented hereinabove are to be taken as illustrative but not limiting. Still other variations in treatment parameters are possible within the spirit and scope of the present claims and will readily present themselves to those skilled in the art.

We claim:

1. A method for treating a patient exhibiting left ventricular dysfunction and having a left ventricular ejection fraction of no more than about 40 percent of left ventricle volume, but at least 15 percent of left ventricle volume, which comprises applying, during diastole, for a time period of about one hour, about five days each week for at least about seven weeks, an incrementally increasing external therapeutic pressure using a plurality of cuffs, sequentially to the lower extremities of the patient, beginning with a first hourly treatment at a D/S Ratio in the range of about 0.4:1 up to about 0.6:1 and thereafter at a D/S Ratio in the range of about 0.5:1 to about 1:1 for each consecutive hourly treatment, with the proviso that the average D/S Ratio over the entire treatment does not exceed about 0.9:1.

2. A method in accordance with claim 1 wherein the left ventricular ejection fraction is in the range of 15 percent to about 20 percent of left ventricular volume, and during diastole, for a time period of about one hour, about five days each week for about seven weeks, an incrementally increasing external therapeutic pressure is applied, sequentially to lower extremities of the patient, in the following sequence:

at a therapeutic pressure of about 90 up to 120 mmHg to produce a D/S Ratio of about 0.4:1 for the initial one-hour treatment;

at an increased therapeutic pressure of about 120 mmHg up to 150 mmHg to effect a D/S Ratio of about 0.5:1 for the next four one-hour treatments;

at an increased therapeutic pressure sufficient to maintain a D/S Ratio of about 0.7:1 for the next fifteen, one-hour treatments; and thereafter at an increased therapeutic pressure sufficient to maintain a D/S Ratio of about 0.8:1 for at least an additional fifteen one-hour treatments.

3. A method in accordance with claim 1 wherein the left ventricular ejection fraction is in the range of about 20 percent to about 30 percent of left ventricular volume, and during diastole, for a time period of about one hour, about five days each week for about seven weeks, an incrementally increasing external therapeutic pressure is applied, sequentially to lower extremities of the patient, in the following sequence:

at a therapeutic pressure of about 90 up to 120 mmHg to produce a D/S Ratio of about 0.5:1 for the initial one-hour treatment;

at an increased therapeutic pressure of about 120 up 150 mmHg to effect a D/S Ratio of about 0.6:1 for the next four one-hour treatments;

at an increased therapeutic pressure sufficient to maintain a D/S Ratio of about 0.7:1 for the next fifteen one-hour treatments; and thereafter at an increased therapeutic pressure sufficient to maintain a D/S Ratio of about 0.8:1 for at least an additional fifteen one-hour treatments.

4. A method in accordance with claim 1, wherein the left ventricular ejection fraction is in the range of about 30 percent to about 40 percent of left ventricular volume, and during diastole, for a time period of about one hour, about five days each week for about seven weeks, an incrementally increasing external therapeutic pressure is applied, sequentially to lower extremities of the patient, in the following sequence:

at a therapeutic pressure of about 90 up to 120 mmHg to effect a D/S Ratio of about 0.6:1 for the initial one-hour treatment;

at an increased therapeutic pressure of about 120 up to 150 mmHg to produce a D/S Ratio of about 0.7:1 for the next four one-hour treatments;

at an increased therapeutic pressure sufficient to maintain a D/S Ratio of about 0.8:1 for the next fifteen one-hour treatments; and thereafter at an increased therapeutic pressure sufficient to maintain a D/S Ratio of about 0.9:1 for at least an additional fifteen one-hour treatments.

5. The method in accordance with claim 1 for treating congestive heart failure.

6. The method in accordance with claim 1 for treating cardiomyopathy.

7. The method in accordance with claim 1 for treating post-heart transplant cardiac dysfunction.

8. The method in accordance with claim 1 for treating post-cardiac arrest cardiac dysfunction.

9. The method in accordance with claim 1 for treating heart trauma.

10. The method in accordance with claim 1 for treating a heart infection.

11. The method in accordance with claim 1 for treating post-acute myocardial infarction cardiac dysfunction.

12. The method in accordance with claim 1 for treating heart transplant candidates waiting for a biocompatible donor heart.

13. The method in accordance with claim 1 wherein the increased external therapeutic pressure is applied sequentially first to the calves, next to the thighs and then to the buttocks of the patient.

* * * * *